(12) United States Patent
Mulholland

(10) Patent No.: US 6,283,940 B1
(45) Date of Patent: Sep. 4, 2001

(54) CATHETER

(76) Inventor: S. Grant Mulholland, 1783 Sheeder Mill Rd., P.O. Box 20, Birchrunville, PA (US) 19421-0020

( * ) Notice: Subject to any disclaimer, the term of this patent is extended or adjusted under 35 U.S.C. 154(b) by 0 days.

(21) Appl. No.: 08/920,529

(22) Filed: Aug. 29, 1997

(51) Int. Cl.$^7$ ............................ A61M 29/00; A61M 5/00; A61M 27/00; A61B 1/32

(52) U.S. Cl. ....................... 604/96.01; 604/104; 604/246; 604/544; 604/105; 606/198; 600/208; 600/207

(58) Field of Search ..................... 604/96–99, 104–106, 604/246, 247, 264, 280, 101, 544; 606/191, 192, 198; 600/207, 208

(56) References Cited

U.S. PATENT DOCUMENTS

| | | | |
|---|---|---|---|
| 4,245,639 | * | 1/1981 | La Rosa . |
| 4,248,235 | * | 2/1981 | Taylor . |
| 4,327,720 | * | 5/1982 | Bronson et al. . |
| 5,193,533 | * | 3/1993 | Body et al. . |
| 5,275,610 | * | 1/1994 | Eberbach . |
| 5,383,856 | * | 1/1995 | Berish ................................. 604/101 |
| 5,437,638 | * | 8/1995 | Bowman .............................. 604/101 |
| 5,441,485 | * | 8/1995 | Peters .................................. 604/101 |
| 5,501,669 | * | 3/1996 | Conway et al. . |
| 5,505,702 | * | 4/1996 | Arney .................................. 604/101 |
| 5,522,790 | * | 6/1996 | Moll et al. . |
| 5,613,950 | * | 3/1997 | Yoon . |
| 5,669,879 | * | 9/1997 | Duer . |
| 5,713,853 | * | 2/1998 | Clark et al. . |
| 5,776,047 | * | 7/1998 | Fukunaga et al. ................... 604/101 |
| 6,027,519 | * | 2/2000 | Stanford .............................. 606/198 |

OTHER PUBLICATIONS

The Foley Catheter, Dover (Registered), Silicone Elastomer Coated 16 Fr., 5 cc—Physical Specimen Date unknown, however, Applicant concedes that this physical specimen is prior art to the present invention.

The Mallacote Catheter or Mushroom Catheter, 26 Bardex UW4 860—Physical Sepcimen Date unknown, however, Applicant concedes that this physical specimen is prior art to the present invention.

\* cited by examiner

*Primary Examiner*—Angela D. Sykes
(74) *Attorney, Agent, or Firm*—Synnestvedt & Lechner LLP

(57) ABSTRACT

A catheter for insertion into a cavity, duct, or vessel to permit injection or withdrawal of fluids or to establish patency of a passageway comprises an elongated tubular catheter body having a distal end and a proximal end and an outer diameter, a drainage lumen extending through the catheter body from the distal end to the proximal end, the drainage lumen communicating with an opening in the catheter body at the distal end of the catheter body, an inflation lumen formed in the catheter body, and one or more of the following: a) inflatable tube sections disposed on the catheter body at the distal end of the catheter body for securing the distal end of the catheter body in a desired location when the tube sections are inflated, b) a valve connected to the inflation lumen for permitting backflow of the inflation fluid from the inflation lumen through the valve when a pre-set pressure value is reached, and c) a hollow reservoir for holding a pre-determined volume of inflation fluid.

18 Claims, 3 Drawing Sheets

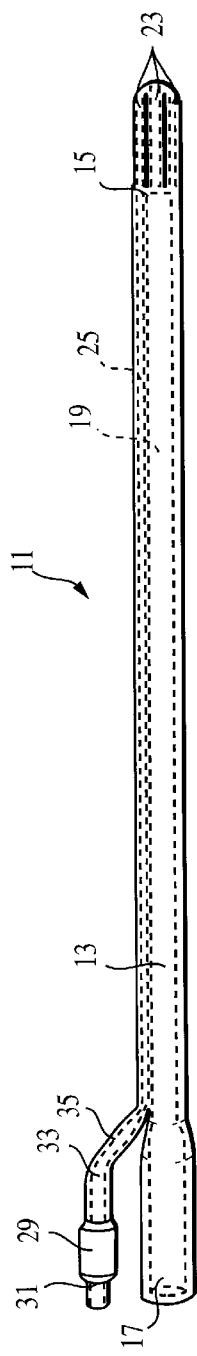
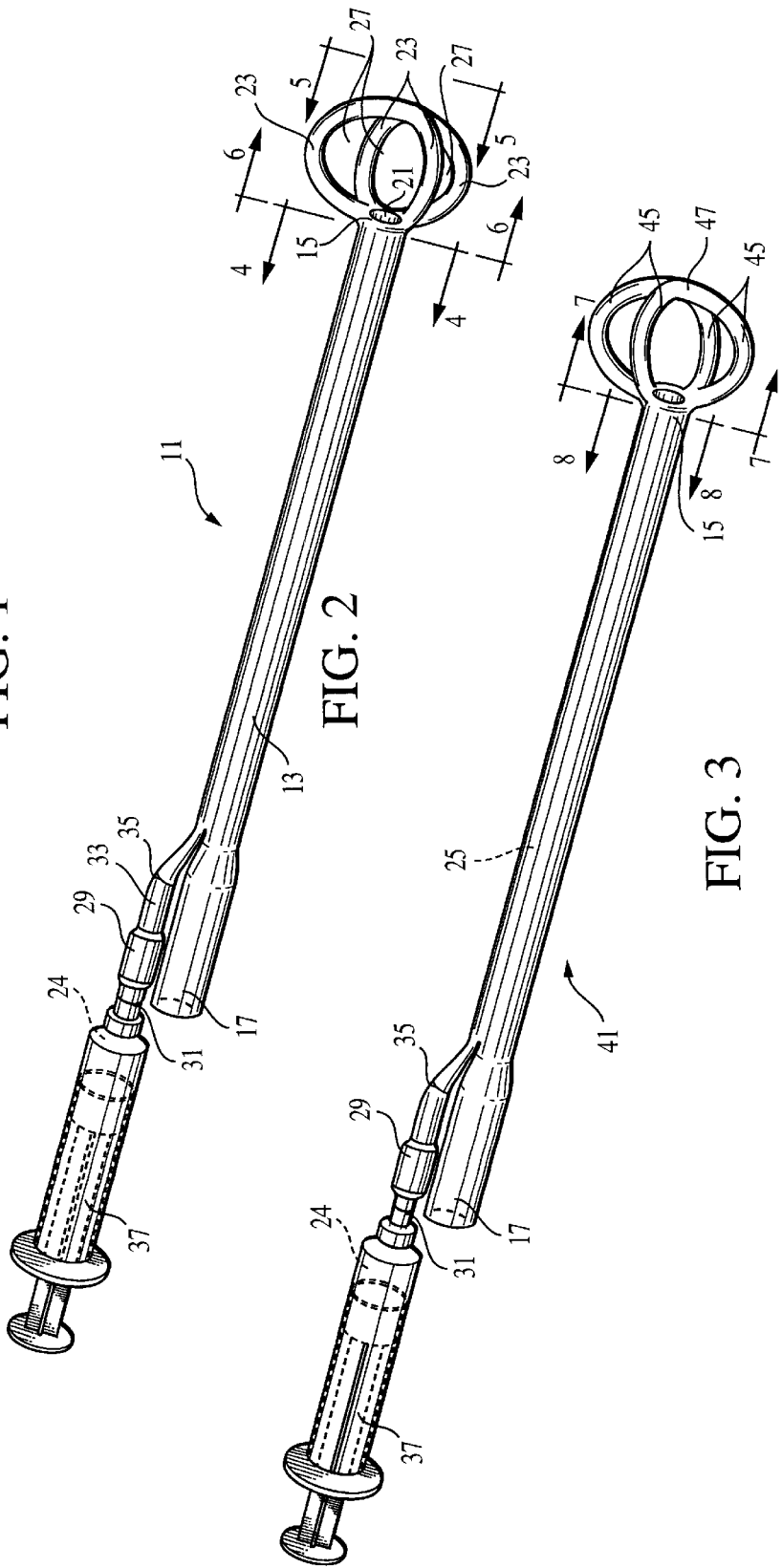

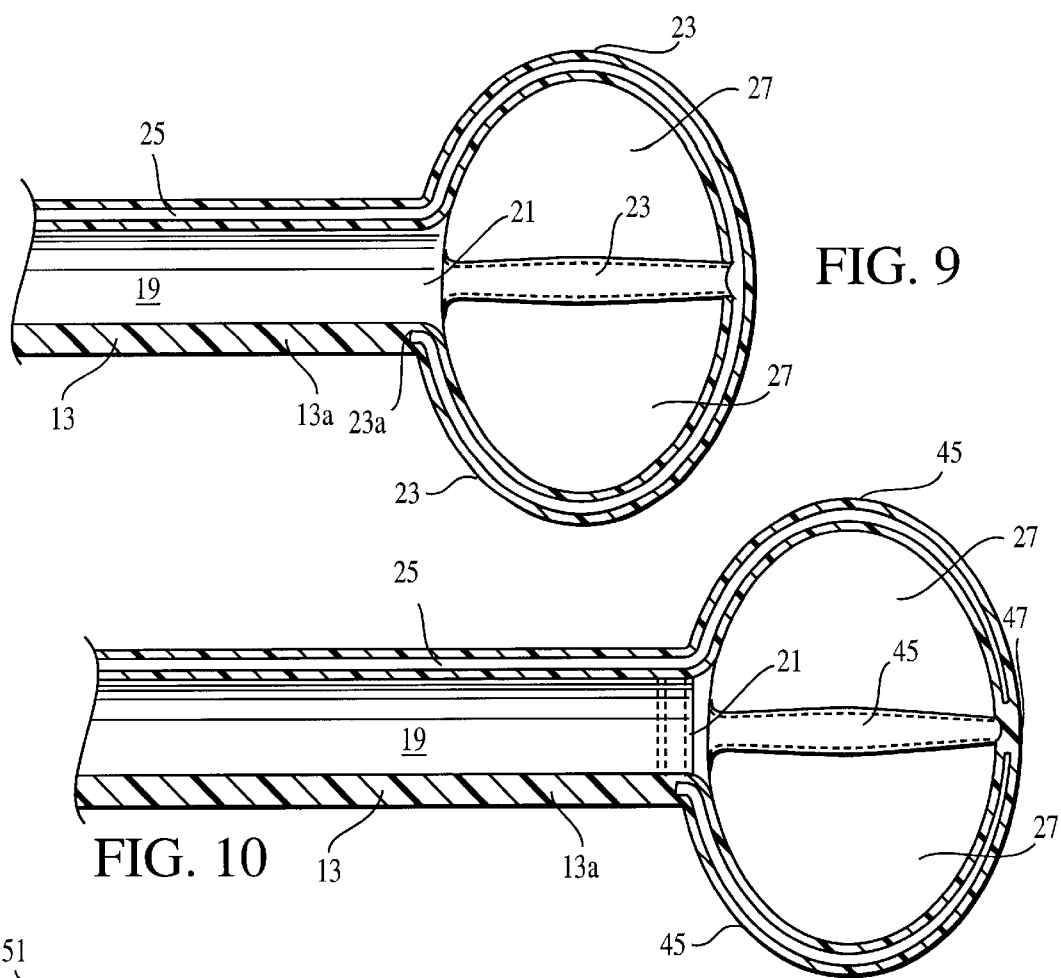
FIG. 9
FIG. 10
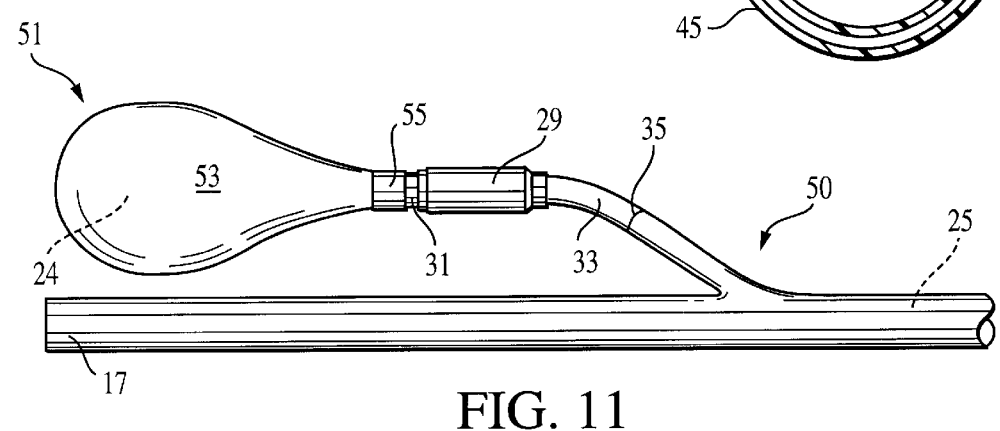
FIG. 11
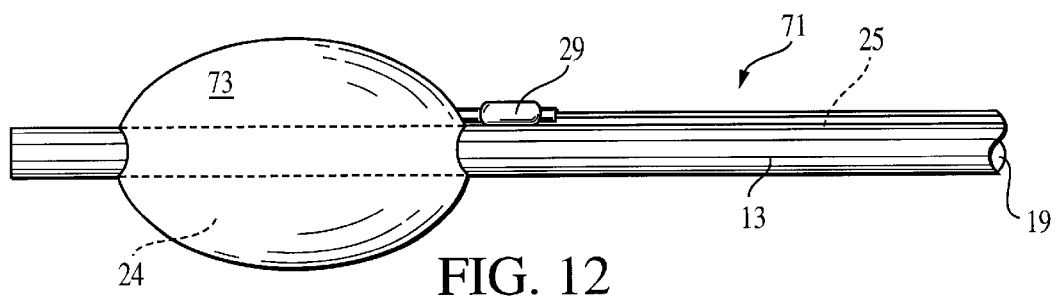
FIG. 12

CATHETER

BACKGROUND OF THE INVENTION

1. Field of the Invention

This invention relates to catheters for insertion into a cavity, duct, or vessel to permit injection or withdrawal of fluids or to establish patency of a passageway, and especially relates to a urinary catheter for insertion through a person's urethra and into a person's bladder for draining urine from the bladder and/or injecting irrigation fluid into the bladder.

2. Description of the Prior Art

The Foley catheter has found wide-spread use for decades as a urinary catheter. The Foley catheter comprises an elongated tubular catheter body having a distal end and a proximal end, and a drainage lumen extending through the catheter body from just short of the distal end to the proximal end. An opening or eyelet is provided in the catheter body just short of the distal end of the catheter body to permit urine to drain from a patient's bladder into the drainage lumen, as well as to permit irrigation fluid to flow from the drainage lumen into a person's bladder when it is desired to irrigate the patient's bladder.

The Foley catheter is provided with an inflatable retaining balloon near the distal end of the catheter body, located short of the opening to the drainage lumen, for securing the distal end of the catheter body in the patient's bladder. The retaining balloon is filled by injecting fluid with a syringe through a small filling channel. The fluid is retained by a valve which closes after removal of the syringe.

A problem with the Foley catheter is that pooling of urine and other fluids within a patient's bladder often occurs due to improper design. This urine pooling problem occurs because good drainage of urine from a patient's bladder is often difficult or impossible using a Foley catheter. Due to the structure of the Foley catheter, the opening to the drainage lumen is positioned above or away from the entrance to the patient's urethra when the distal end of the catheter body is retained in a patient's bladder since the opening to the drainage lumen is positioned between the retaining balloon and the distal end of the catheter body. Similarly, due to the structure of the Foley catheter, properly irrigating a patient's bladder using a Foley catheter is often difficult.

Another problem with the Foley catheter is that the tip or nipple portion of the Foley catheter sometimes irritates the patient's bladder.

Another problem with the Foley catheter is that severe injury may occur to a patient if the catheter is removed from the patient's bladder before the retaining balloon is deflated.

Another type of catheter is called the "Mallacote" catheter or mushroom catheter. This catheter has a drainage lumen extending through its elongated tubular body, and a "web-like" retaining structure near its distal end for securing the distal end of the catheter body in a patient's bladder. However, the catheter requires a stylet to be used to flatten the web-like retaining structure when inserting the distal end of the catheter body through the patient's urethra and into the patient's bladder. Further, "web-like" retaining structure is flexible and can easily collapse if the catheter is pulled on, resulting in the catheter not staying in place. This type of catheter also has a tip at its distal end which sometimes irritates the patient's bladder.

SUMMARY OF THE INVENTION

It is an object of the invention to provide a catheter that permits superior drainage so as to avoid the problem of pooling of urine in a patient's bladder which often occurs using a Foley catheter.

Another object of the invention is to provide a catheter that facilitates good irrigation of a patient's bladder.

Another object of the invention is to provide a catheter having a smooth tip at its distal end to avoid irritation of a patient's bladder as often happens due to the structure at the distal end of a Foley catheter and a Mallacote catheter.

Another object of the invention is to provide a catheter having a retaining member at its distal end which properly retains the distal end of the catheter in a patient's bladder during normal use, but permits easy removal of the catheter from the patient's bladder when the catheter is accidentally removed from the patient's bladder, thereby avoiding injury to the patient's urethra.

Another object of the invention is to provide a catheter having a hollow reservoir for holding a pre-determined volume of inflation fluid to avoid a problem of overinflating or underinflating a retaining member at the distal end of the catheter and to avoid the need for a syringe to inflate the retaining member.

These and other objects are accomplished by my invention which is described below.

BRIEF DESCRIPTION OF THE DRAWINGS

FIG. 1 is a view in front elevation of a catheter constructed in accordance with the invention;

FIG. 2 is a perspective view of the catheter shown in FIG. 1, with its web-like retaining member or retaining tube sections being inflated;

FIG. 3 is a perspective view of an alternative embodiment of the inventive catheter;

FIG. 9 is a view in cross section of the tube section 23 and the distal end 15 of the catheter 11 shown in FIG. 2;

FIG. 10 is a view in cross section of the tube section 45 and the distal end 15 of the catheter 11 shown in FIG. 3;

FIG. 11 is a partial view in elevation of a catheter provided with a reservoir, constructed in accordance with the invention; and FIG. 12 is a partial view in elevation of another catheter provided with a reservoir, constructed in accordance with the invention.

DETAILED DESCRIPTION OF THE DRAWING

Figure 4:
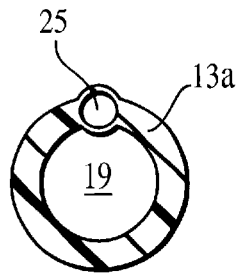
FIG. 4 is a cross sectional view taken along the lines and arrows 4—4 in FIG. 2.
Figure 5:
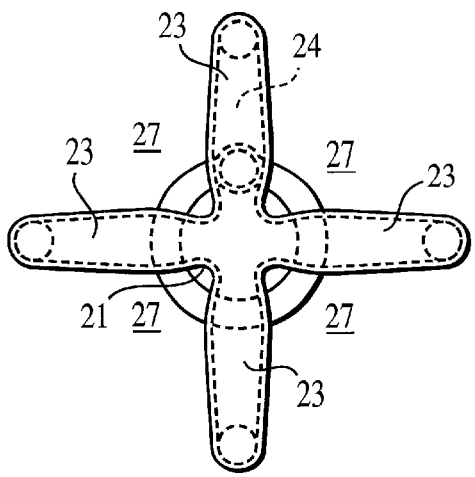
FIG. 5 is a cross sectional view taken along the lines and arrows 5—5 in FIG. 2.

Turning to the drawings, there shown in FIGS. 1–2 a catheter 11 for insertion into a cavity, duct, or a vessel to permit injection or withdrawal of fluids into or from the cavity, duct, or vessel, or to establish patency of a passageway. For example, catheter 11 may be inserted through a patient's urethra and into the patient's bladder for draining urine from the bladder and/or injecting irrigation fluid into the bladder.

Catheter 11 includes an elongated tubular catheter body 13 having a distal end 15 and a proximal end 17.

Referring to FIGS. 1, 2, and 9, a drainage lumen 19 extends through the catheter body 13 from the distal end 15 to the proximal end 17, and the drainage lumen 19 communicates with an opening 21 in the catheter body 13 at the distal end 15 of the catheter body 13 through which the fluid may flow into the drainage lumen 19 when the catheter 11 is used to drain a fluid from a cavity, duct, or vessel (e.g., draining urine from a person's bladder) and through which fluid may flow from the drainage lumen 19 when the catheter 11 is used to inject a fluid into a cavity, duct, or vessel (e.g., injecting irrigation fluid into a person's bladder).

Referring to FIGS. 2, 5, 6, and 9, a plurality of hollow inflatable tube sections 23, four being shown in this embodiment of the invention, are disposed on the catheter body 13 at the distal end 15 of the catheter body 13 for securing the distal end 15 of the catheter body 13 in a desired location in the cavity, duct, or vessel (i.e., a person's bladder) when the tube sections 23 are inflated.

Referring to FIGS. 1 and 9, an inflation lumen 25 extends along the length of the catheter body 13 in the catheter body wall 13a (FIG. 4) and communicates with the inflatable tube sections 23. Inflation fluid 24, such as distilled water, is passed through inflation lumen 25 into the tube sections 23 to inflate the tube sections 23, and the inflation fluid 24 is withdrawn from the tube sections 23 into and through the inflation lumen 25 when it is desired to deflate the tube sections 23.

When the inflatable tube sections 23 are not inflated, they lie substantially parallel to one another along the central axis of the catheter body 13 as shown in FIG. 1, forming a cylinder having a diameter that substantially matches the outer diameter of the catheter body 13.

Figure 6:
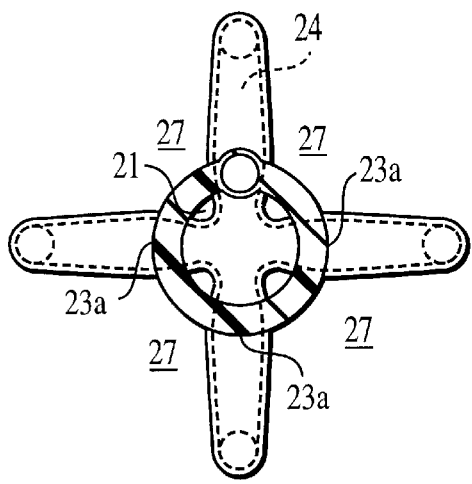
FIG. 6 is a cross sectional view taken along the lines and arrows 6—6 in FIG. 2.
Figure 7:
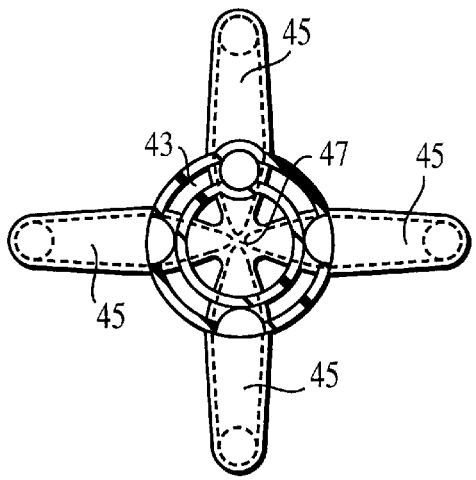
FIG. 7 is a cross sectional view taken along the lines and arrows 7—7 in FIG. 3.
Figure 8:
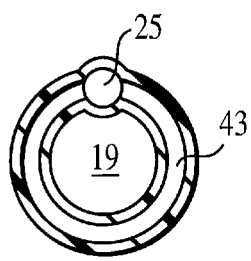
FIG. 8 is a cross sectional view taken along the lines and arrows 8—8 in FIG. 3.

As shown in FIGS. 6 and 9, the end portion 23a of each tube section 23, except the tube section 23 being directly fed by the inflation lumen 25, connecting the tube section 23 to the distal end 15 of the catheter body 13 is closed.

Referring to FIGS. 2, 5, 6, and 9, when the tube sections 23 are inflated, the tube sections 23 bow outwardly away from each other and away from the central axis of the catheter body 13 creating passageways 27 between each adjacent bowed tube section 23 for fluid, such as urine, to flow through and into the drainage lumen 19 through opening 21. Likewise, when tube sections 23 are inflated, fluid, such as irrigating fluid, may easily flow from the drainage lumen 19 through the opening 21 and the passageways 27 into a person's bladder, for example, when the catheter 11 is being used as a urinary catheter.

In the embodiment of the invention shown in FIGS. 1, 2, 4–6, and 9, the four tube sections 23 bow outwardly when inflated, as shown in FIGS. 2, 5, 6, and 9, to form a substantially hollow sphere having a diameter that is substantially larger than the diameter of the catheter body 13. When the catheter 11 is being used as a urinary catheter, the hollow sphere formed by inflating tube sections 23 secures the distal end 15 of the catheter body in a person's bladder by blocking the removal of the distal end 15 of the catheter 11 into a person's urethra.

As shown in FIGS. 1 and 2, catheter 11 is provided with a valve 29 positioned at an inflation port 31 formed in the catheter body 13 through which inflation fluid 24 is passed into the inflation lumen 25. The valve 29 is constructed to permit insertion of inflation fluid 24 into the inflation lumen 25 and subsequently to the inflatable tube sections 23 and for preventing backflow of the inflation fluid 24 from the inflation lumen 25 during normal operation of the catheter 11. An exemplary valve 29 is that made by Bard, but other companies make such valves.

Alternatively and preferably, valve 29 also permits backflow of the inflation fluid from the inflation lumen 25 through the valve 29 if a pre-set pressure value is reached. That is, the valve 29 preferably is of the type that permits backflow of the inflation fluid 24 from the inflation lumen 25 through the valve 29 when a pre-set pressure level is reached, such as the pressure level reached when it is attempted to remove the catheter 11 from its secured position while the inflatable tube sections 23 are inflated, or when it is attempted to inflate the inflatable tube sections 23 while they are positioned in a location, such as the urethra, that is too small to receive the distal end 15 of the catheter 11 when the inflatable tube sections 23 are inflated.

Since the preferred valve 29 permits backflow when a pre-set pressure release level is reached, the pre-set pressure release level being at or just below the amount of pressure created in the inflation lumen 25 and the tube sections 23 when attempting to remove the inventive catheter 11 from a person's bladder while the tube sections 23 of the invention are inflated, the risk of injury to a person's urethra associated with accidental removal of a Foley catheter from a person's bladder while the balloon of the Foley catheter is inflated is eliminated with the inventive catheter 11.

Similarly, the risk of injury to a person's urethra associated with accidentally inflating the balloon of a Foley catheter when the distal end of the Foley catheter is still in the urethra and not yet in the person's bladder is eliminated with the inventive catheter 11 since the pre-set pressure release level of the valve 29 is reached when it is attempted to inflate the tubes sections 23 in a location that is too small to receive the tube sections 23 when inflated, such as in a person's urethra, thereby avoiding inflation of the tube sections 23 while the tube sections are in the urethra.

Valve 29, having the characteristics set out above, including the characteristic of a safety release at a pre-set pressure value, may be a component part of the inventive catheter 11, the inventive catheters 41, 50, and 71 to be described below, or other catheters such as a Foley catheter.

Catheter 11 is made by a latex dipping process used commonly today to make Foley catheters. The tubular portion of catheter body 13 is made by repeatedly dipping a rod into latex to form the tubular portion around the rod. The tube sections 23 and a tube member comprising the inflation lumen 25 and the side arm 33 are made in a similar fashion.

The tube sections 23, and the tube member comprising inflation lumen 25 and the side arm 33 are removed from the rods, the tube sections 23 and the tube member comprising the inflation lumen 25 and the side arm 33 are welded onto the tubular portion such that the tube member comprising the inflation lumen 25 becomes part of the catheter body wall 13a and the inflation lumen 25 feeds into one of the tube sections 23.

In use, catheter 11 is inserted into a cavity, duct, or vessel. For example, if the catheter 11 is being used as a urinary catheter, the catheter body 13 is inserted through a person's urethra and into a person's bladder such that the distal end 15 of the catheter body 13, along with the tube sections 23, are located in the person's bladder and the main portion of the catheter body 13 is located in the person's urethra. Then, inflation fluid 24 is inserted from a syringe 37 into the inflation lumen 25 through the port 31 to the tube sections 23 to inflate the tube sections 23, thereby securing the distal end 15 of the catheter 11 in place in the persons'bladder.

Urine may then drain from the person's bladder by moving through passageways 27 between the adjacent tube sections 23 and into the opening 21 to the drainage lumen 19 through which the urine may flow to a waste collection bag located at the proximal end 17 of the catheter body 13.

When it is desired to remove the catheter 11 from where it is secured (e.g., from a person's bladder), the tube sections 23 may be deflated by cutting the side arm 33 of the catheter body 13 and draining the inflation lumen 25. The cut in the side arm 33 must be before the valve 29 if the catheter 11 is provided with a valve 29, such as along dotted line 35 shown in FIGS. 1 and 2. Alternatively, the inflation lumen 25 may be drained by overriding the valve 29 or by opening the valve 29 with a syringe and draining the inflation fluid 24 through the valve 29 into the syringe.

FIGS. 3, 7, 8, and 10 show an alternative embodiment of the invention, catheter 41. Catheter 41 is substantially the same as catheter 11, except that inflation lumen 25 of catheter 41 flows into a ring-shaped channel 43, as shown in detail in FIGS. 7, 8, and 10, formed in the distal end 15 of catheter 41, and hollow inflatable tube sections 45 communicate with the channel 43. The ring-shaped channel 43 acts as common channel to which the inflatable tube sections 45 connect. In this embodiment of the invention, the tube sections 45 are inflated by passing the inflation fluid 24 through the port 31 into the inflation lumen 25 to fill the inflation lumen 25, the channel 43, and the inflatable tube sections 45. Preferably, the end portions 47 of the tube sections 45 are closed.

Catheter 41 also is made using latex dipping process, and a catheter 41 is used in the same manner as catheter 11.

Turning now to FIG. 11, there is shown a catheter 50 having a hollow reservoir 51 mounted on the port 31 of the inflation lumen 25 for holding a pre-determined volume of inflation fluid 24. The reservoir 51 comprises a hollow ball portion 53 for holding the inflation fluid 24, and a port member 55 extending from the ball portion 53 from which the inflation fluid 24 flows from the ball portion 53. The reservoir 51 is mounted on the inflation port 31 of the catheter body 13 using an interference fit between the outer surface area of the inflation port 31 and the inner surface portion of reservoir port member 55.

The reservoir 51 is made from latex, or other suitable material.

In use, the reservoir ball portion 53 is squeezed to force the inflation fluid 24 from the reservoir ball portion 53 through the port member 55 of the reservoir 51 and into the inflation lumen 25 to the retaining member (e.g., the tube sections 23, 45) to inflate the retaining member to secure the distal end of the catheter in a desired location (e.g., a person's bladder).

When it is desired to remove the catheter 50 provided with the reservoir 51 from where it is secured (e.g., from a person's bladder), the retaining member may be deflated by cutting the side arm 33 of the catheter body 13 and draining the inflation lumen 25. The cut in the side arm 33 must be before the valve 29, such as along dotted line 35 shown in FIG. 11. Alternatively, the inflation lumen 25 may be drained by overriding the valve 29, or by squeezing valve 29 which opens the valve and allows fluid to flow back into the reservoir.

Reservoir 51 may be a component part of the inventive catheters 11, 41, and 50, or other catheters such as a Foley catheter.

Preferably, the reservoir 51 is provided with a pre-determined volume of inflation fluid 24. The pre-determined volume of inflation fluid is the volume needed to permit correct operation of the inflatable tube sections 23, 45. Because the reservoir contains the exact amount of fluid needed to inflate the tube sections 23, 45, the problem of overfilling or underfilling the retaining member (e.g., the tube sections 23, 45) does not occur, unlike with catheters that use a syringe to inflate the retaining member.

FIG. 12 shows an alternative embodiment of the invention, the catheter 71 having a reservoir 73 for holding a pre-determined volume of inflation fluid 24. Reservoir 73 is integral with catheter 71 and has a somewhat flattened hollow spherical shape with the drainage lumen 19 extending through its center.

Catheter 71 also is made by using a latex dipping process, and reservoir 73 is formed, filled with inflation fluid 24, and welded onto the catheter body such that reservoir 73 is connected to the catheter body and feeds into the inflation lumen 25 of catheter 71. In this embodiment, valve 29 is attached to the tube member comprising the inflation lumen 25 before the tube member comprising the inflation lumen 25 is welded onto the tubular portion of the catheter body 13, and during the welding of reservoir 73 onto the catheter body, the reservoir 73 is connected with valve 29.

Catheter 71 is used in substantially the same fashion as catheter 50.

Catheters 11, 41, 50, and 71 may be made from latex, latex with Teflon material, silicone, polyvinyl, Silastic material, and other known materials used to make catheters.

ADVANTAGES

A main advantage of the inventive catheter 11, 41 over the Foley catheter is that the inventive catheter 11, 41 permits more effective drainage and irrigation than the Foley catheter. While pooling of urine in a patient's bladder often occurs using a Foley catheter, this problem is avoided using the inventive catheter 11, 41 since the opening 21 to the drainage lumen 19 is located at the entrance to the patient's urethra, rather than positioned above or away from the entrance to the patient's urethra as with the Foley catheter.

Similarly, the inventive catheter 11, 41 promotes proper irrigation of a patient's bladder due to the location of the entrance or opening 21 to the drainage lumen 19 of the inventive catheter 11, 41. In contrast, it is often difficult to properly irrigate a patient's bladder using a Foley catheter. There is a marked advantage with irrigation using the catheter of my invention. Instead of a small opening or eye at the tip of the Foley catheter, there is a large opening that allows debris, clots, etc. to easily be removed. The bladder wall is commonly sucked into or over the Foley catheter eye with negative pressure which causes discomfort and inability to remove material from the bladder. With the web-like structure of the retaining tube section 23, 45 of my invention, the bladder does not occlude the opening to the drainage lumen.

The inventive catheter 11, 41 has a smooth tip at its distal end to avoid irritation of a patient's bladder as often happens due to the "tip" structure at the distal end of a Foley catheter and a Mallacote catheter.

In contrast to the Foley catheter, a catheter provided with a valve that permits backflow of the inflation fluid from the inflation lumen if a pre-set pressure value is reached, in accordance with the invention, prevents injury to a patient's urethra if it is attempted to remove the catheter from its secured position in the patient's bladder while the inflatable retaining member (e.g. tube sections 23 or a balloon) is inflated, or when it is attempted to inflate a inflatable retaining member in a location (e.g., in a patient's urethra) that is too small to receive the inflatable retaining member when the retaining member is inflated.

In accordance with the invention, a catheter that is provided with a pre-filled reservoir 51, 73 avoids the need of searching for another piece of equipment (i.e., a syringe 37) and inflation fluid 24 to fill the inflatable retaining member, as well as avoiding the problem of overinflating or underinflating a retaining member. Also, such a catheter with a pre-filled reservoir 51, 73 is more economical than the known catheters since no other pieces of equipment and supplies (i.e., a syringe and a separate supply of inflation fluid 24) need be purchased.

What is claimed is:

1. A catheter for insertion into a cavity, duct, or vessel having an opening to permit injection or withdrawal of fluids or to establish patency of a passageway, comprising an elongated tubular catheter body having a distal end, a proximal end, and an outer diameter, a drainage lumen extending through the catheter body from the distal end to the proximal end, the drainage lumen communicating with an opening in the catheter body at the distal end of the catheter body, inflatable tube means disposed on the catheter body at the distal end of the catheter body for securing the opening in the catheter body at the distal end of the catheter body substantially at the opening of the cavity, duct, or vessel when the inflatable tube means is inflated wherein the inflatable tube means comprises a plurality of hollow inflatable tube sections extending in parallel from the distal end of the catheter body axially along a central axis of the catheter body when the hollow inflatable tube sections are not inflated and bowing outwardly away from each other and away from the central axis to form a substantially hollow sphere having a passageway between each adjacent tube section for fluid to and from the opening in the catheter body at the distal end of the catheter body when the inflatable tube means is inflated, an inflation lumen formed in the catheter body and in communication with the inflatable tube means, and an inflation port formed in the catheter body in communication with the inflation lumen, the inflatable tube means being substantially cylindrical when not inflated and having a diameter substantially matching the outer diameter of the catheter body.

2. The catheter of claim 1, further including valve means positioned at the inflation port for permitting insertion of inflation fluid into the inflation lumen and to the inflatable tube means and for preventing backflow of inflation fluid from the inflation lumen during normal operation of the catheter, the valve means including means for permitting backflow of the inflation fluid from the inflation lumen through the valve means if a pre-set pressure value is reached, the pressure value being such that the backflow of inflation fluid from the inflation lumen through the valve means occurs when it is attempted to remove the catheter from its secured position when the inflatable tube means is inflated, or when the inflatable tube means is positioned in a location that is too small to receive the distal end of the catheter when the inflatable tube means is inflated.

3. The catheter of claim 2, further including a hollow reservoir for holding a pre-determined volume of inflation fluid, the reservoir being disposed at the inflation port and separated from the inflation lumen by a valve.

4. The catheter of claim 3, the reservoir comprising a hollow ball member for holding the inflation fluid, and a port member formed on and extending from the hollow ball member from which the inflation fluid flows from the hollow ball member, the port member being mounted on the inflation port of the catheter body.

5. The catheter of claim 3, the reservoir comprising a hollow member having end portions that are integral with the catheter body and having the drainage lumen extending through the hollow member.

6. A catheter for insertion into a cavity, duct, or vessel having an opening to permit injection or withdrawal of fluids or to establish patency of a passageway, comprising an elongated tubular catheter body having a distal end and a proximal end, a drainage lumen extending through the catheter body from the distal end to the proximal end, the drainage lumen communicating with an opening in the catheter body at the distal end of the catheter body, inflatable retaining means disposed on the catheter body at the distal end of the catheter body for retaining the opening in the catheter body at the distal end of the catheter body substantially at the opening of the cavity, duct, or vessel when the inflatable retaining means is inflated wherein the inflatable retaining means comprises a plurality of hollow inflatable tube sections extending in parallel from the distal end of the catheter body axially along a central axis of the catheter body when the hollow inflatable tube sections are not inflated and bowing outwardly away from each other and away from the central axis to form a substantially hollow sphere having a passageway between each adjacent tube section for fluid to and from the opening in the catheter body at the distal end of the catheter body when the inflatable tube means is inflated, an inflation lumen formed in the catheter body and in communication with the inflatable retaining means, an inflation port formed in the catheter body in communication with the inflation lumen, valve means positioned at the inflation port for permitting insertion of inflation fluid into the inflation lumen and to the inflatable retaining means and for preventing backflow of inflation fluid from the inflation lumen during normal operation of the catheter, the valve means including means for permitting backflow of the inflation fluid from the inflation lumen through the valve means if a pre-set pressure value is reached, the pressure valve being such that the backflow of the inflation fluid from the inflation lumen through the valve means occurs when it is attempted to remove the catheter from its secured position when the inflatable retaining means is inflated, or when the inflatable retaining means is positioned in a location that is too small to receive the distal end of the catheter when the inflatable retaining means is inflated.

7. The catheter of claim 6, further including a hollow reservoir for holding a pre-determined volume of inflation fluid, the reservoir being disposed at the inflation port and separated from the inflation lumen by the valve means.

8. The catheter of claim 6, the reservoir comprising a hollow ball member for holding the inflation fluid, and a port member formed on and extending from the hollow ball member from which the inflation fluid flows from the hollow ball member, the port member being mounted on the inflation port of the catheter body.

9. The catheter of claim 6, the reservoir comprising a hollow member having end portions that are integral with the catheter body and having the drainage lumen extending through the hollow member.

10. The catheter of claim 6, further including a pre-determined volume of inflation fluid, the volume being such as to permit correct operation of the inflatable retaining means.

11. A catheter for insertion into a cavity, duct, or vessel having an opening to permit injection or withdrawal of fluids or to establish patency of a passageway, comprising an elongated tubular catheter body having a distal end and a proximal end, a drainage lumen extending through the catheter body from the distal end to the proximal end, the drainage lumen communicating with an opening in the catheter body at the distal end of the catheter body, inflatable retaining means disposed on the catheter body at the distal end of the catheter body for retaining the opening in the catheter body at the distal end of the catheter body substantially at the opening of the cavity, duct, or vessel when the inflatable retaining means is inflated wherein the inflatable retaining means comprises a plurality of hollow inflatable tube sections extending in parallel from the distal end of the catheter body axially along a central axis of the catheter body when the hollow inflatable tube sections are not inflated and bowing outwardly away from each other and away from the central axis to form a substantially hollow sphere having a passageway between each adjacent tube section for fluid to and from the opening in the catheter body at the distal end of the catheter body when the inflatable tube means is inflated, an inflation lumen formed in the catheter body and in communication with the inflatable retaining means, an inflation port formed in the catheter body in communication with the inflation lumen, and, a hollow reservoir for holding a pre-determined volume of inflation fluid, the reservoir being disposed at the inflation port and separated from the inflation lumen by a valve.

12. The catheter of claim 11, the reservoir comprising a hollow ball member for holding the inflation fluid, and a port member formed on and extending from the hollow ball member from which the inflation fluid flows from the hollow ball member, the port member being mounted on the inflation port of the catheter body.

13. The catheter of claim 11, the reservoir comprising a hollow member having end portions that are integral with the catheter body and having the drainage lumen extending through the hollow member.

14. The catheter of claim 11, further including a pre-determined volume of inflation fluid, the volume being such as to permit correct operation of the inflation retaining means.

15. A urinary catheter for insertion through a person's urethra, past the entrance of the person's urethra and into the person's bladder for draining urine from the bladder and/or injecting irrigation fluid into the bladder, comprising an elongated tubular catheter body having a distal end, a proximal end, and an outer diameter, a drainage lumen extending through the catheter body from the distal end to the proximal end for draining urine from a person's bladder, the drainage lumen communicating with an opening in the catheter body at the distal end of the catheter body, inflatable tube means disposed on the catheter body at the distal end of the catheter body for securing the opening in the catheter body at the distal end of the catheter body substantially at the entrance of the person's bladder by presenting an interference with a portion of the person's bladder at the person's urethra when the inflatable tube means is inflated for resisting removal of the distal end of the catheter body from the bladder wherein the inflatable tube means comprises a plurality of hollow inflatable tube sections extending in parallel from the distal end of the catheter body axially along a central axis of the catheter body when the hollow inflatable tube sections are not inflated and bowing outwardly away from each other and away from the central axis to form a substantially hollow sphere having a passageway between each adjacent tube section for fluid to and from the opening in the catheter body at the distal end of the catheter body when the inflatable tube means is inflated, an inflation lumen formed in the catheter body and in communication with the inflatable tube means, and an inflation port formed in the catheter body in communication with the inflation lumen, the inflatable tube means being substantially cylindrical when not inflated and having a diameter substantially matching the outer diameter of the catheter body.

16. The urinary catheter of claim 15, further including valve means positioned at the inflation port for permitting insertion of inflation fluid into the inflation lumen and to the inflatable tube means and for preventing backflow of inflation fluid from the inflation lumen during normal operation of the catheter, the valve means including means for permitting backflow of the inflation fluid from the inflation lumen through the valve means if a pre-set pressure value is reached, and the pressure value being such that the backflow of inflation fluid from the inflation lumen through the valve means occurs when it is attempted to remove the catheter from its secured position when the inflatable tube means is inflated, or when the inflatable tube means is positioned in a location that is too small to receive the distal end of the catheter when the inflatable tube means is inflated.

17. The urinary catheter of claim 15, further including a hollow reservoir for holding a pre-determined volume of inflation fluid, the reservoir being disposed at the inflation port and separated from the inflation lumen by the valve means, and a pre-determined volume of inflation fluid, the volume being such as to permit correct operation of the inflation tube means.

18. The urinary catheter of claim 15, further including valve means positioned at the inflation port for permitting insertion of inflation fluid into the inflation lumen and to the plurality of tube sections and for preventing backflow of inflation fluid from the inflation lumen during normal operation of the catheter, the valve means including means for permitting backflow of the inflation fluid from the inflation lumen through the valve means if a pre-set pressure value is reached, and the pressure value being such that the backflow of inflation fluid from the inflation lumen through the valve means occurs when it is attempted to be remove the catheter from its secured position when the plurality of tube sections are inflated, or when the plurality of tube sections are positioned in a location that is too small to receive the distal end of the catheter when the plurality of tube sections are inflated, a hollow reservoir for holding a pre-determined volume of inflation fluid, the reservoir being disposed at the inflation port and separated from the inflation lumen by the valve means, and a pre-determined volume of inflation fluid, the volume being such as to permit correct operation of the plurality of tube sections.

* * * * *